United States Patent [19]
Wolfbeis et al.

[11] Patent Number: 6,046,055
[45] Date of Patent: Apr. 4, 2000

[54] LUMINESCENCE-OPTICAL METHOD AND SENSOR LAYER FOR QUANTITATIVE DETERMINATION OF AT LEAST ONE CHEMICAL COMPONENT OF A GASEOUS OR LIQUID SAMPLE

[75] Inventors: Otto S. Wolfbeis; Tobias Werner; Ingo Klimant; Ute Kosch, all of Regensburg, Germany; Marco Jean-Pierre Leiner, Graz, Austria

[73] Assignee: AVL Medical Instruments AG, Schaffhausen, Switzerland

[21] Appl. No.: 09/280,073

[22] Filed: Mar. 29, 1999

Related U.S. Application Data

[62] Division of application No. 08/950,373, Oct. 14, 1997, Pat. No. 5,942,189.

[30] Foreign Application Priority Data

Oct. 16, 1996 [AT] Austria .................................. 1818/96

[51] Int. Cl.[7] .......................... G01N 21/76; G01N 21/64
[52] U.S. Cl. ...................... 436/172; 422/82.07; 422/58; 422/82.08
[58] Field of Search .............................. 422/82.08, 87.07, 422/58; 436/172

[56] References Cited

U.S. PATENT DOCUMENTS

| 4,645,744 | 2/1987 | Charlton et al. ...................... 436/74 |
|---|---|---|
| 4,762,799 | 8/1988 | Seitz et al. ............................ 436/79 |
| 5,037,615 | 8/1991 | Kane ................................. 422/82.08 |
| 5,565,328 | 10/1996 | Bascomb et al. ..................... 435/25 |
| 5,631,169 | 5/1997 | Lakowicz et al. .................. 436/537 |
| 5,776,782 | 7/1998 | Tsuji ................................... 436/171 |
| 5,849,489 | 12/1998 | Heller ..................................... 435/6 |

FOREIGN PATENT DOCUMENTS

| 393035 | 7/1991 | Austria . |
|---|---|---|
| 214768 A2 | 3/1987 | European Pat. Off. . |
| 461392 A2 | 12/1991 | European Pat. Off. . |
| 358991 B1 | 2/1994 | European Pat. Off. . |

OTHER PUBLICATIONS

Jordan et al., Analytical Chemistry 59, 437–439, 1987.
Yuan et al., Journal of Fluorescence, vol. 2, No. 4, pp. 231–235, 1992.
Silva et al., New J. Chemistry, 20,, 871–880, 1996.
Stufkens et al., Coordination Chemistry Reviews, 177, 127–179, 1998.
Kosch et al., Analytical Chemistry, 70, 3892–3897, 1998.
Preininger, Journal of Fluorescence, vol. 8, No. 3, pp. 199–205, 1998.

*Primary Examiner*—Randy Gulakowski
*Assistant Examiner*—Paul J. Lee
*Attorney, Agent, or Firm*—Watson Cole Grindle Watson, P.L.L.C.

[57] ABSTRACT

In a sensor layer for quantitative determination of at least one chemical component in a gaseous or liquid sample medium containing a chromophore which is directly or indirectly responsive to the component being determined by changing its absorption spectrum, and a luminophore which is not responsive to the component being determined, where there is an at least partial overlap between the emission spectrum of the luminophore and the absorption spectrum of the chromophore, and where the energy transfer between luminophore and chromophore produces a measurable change in at least one luminescence characteristic of the luminophore, the luminophore L and the chromophore Γ are ionic substances with differing electrical charges, which are incorporated in a matrix material that is permeable to the chemical component being determined.

5 Claims, 2 Drawing Sheets

LUMINESCENCE-OPTICAL METHOD AND SENSOR LAYER FOR QUANTITATIVE DETERMINATION OF AT LEAST ONE CHEMICAL COMPONENT OF A GASEOUS OR LIQUID SAMPLE

CROSS-REFERENCE TO RELATED APPLICATION

This application is a divisional of application Ser. No. 08/950,373, filed Oct. 14, 1997, now U.S. Pat. No. 5,942,189.

BACKGROUND OF THE INVENTION

The invention relates to a sensor layer for quantitative determination of at least one chemical component of a gaseous or liquid sample containing a chromophore which is directly or indirectly responsive to the component being determined by changing its absorption spectrum and a luminophore which is not responsive to the component being determined, where there is an at least partial overlap of the emission spectrum of the luminophore and the absorption spectrum of the chromophore, and where the energy transfer between luminophore and chromophore effects a measurable change in at least one luminescence characteristic of the luminophore.

In the following luminophores are understood as dyes which emit phosphorescence or fluorescence radiation upon suitable excitation. The absorption spectrum of the chromophore is influenced either directly by the component being measured or indirectly by a chemical reaction product of the component being measured. The term "quantitative determination of a chemical component" refers to the determination of concentration and activity as well as gas partial pressure, the values of luminescence decay time or luminescence intensity of the luminophore being used to infer the measured quantity.

BRIEF DESCRIPTION OF THE DRAWINGS

As a recap.

DESCRIPTION OF THE PRIOR ART

Figure 1:
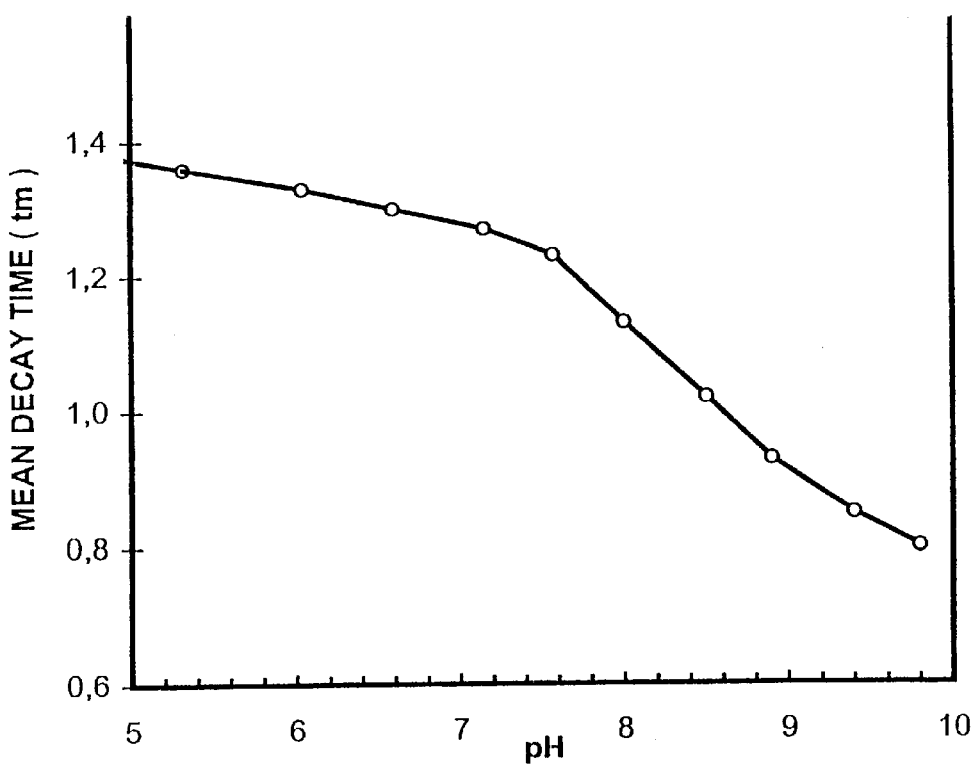
FIG. 1 displays the dependence of mean decay time $t_m$ on the pH value of the sample medium of Example 1.

The above sensor layer is based on a method described in AT 393 035, in which pH- and cation-sensitive chromophores (acceptor) are attached, preferably covalently, to a luminophore (donor). The luminescence decay time of the luminophore is employed for determining the pi value and concentration of the cation being determined in the sample medium.

A similar method is known from EP-A 214 768, where the concentration of the parameter being determined is inferred from the luminescence intensity measured.

The rate of nonradiative energy transfer of donor and acceptor molecules depends on the spatial proximity of the molecules of the two substances. As a consequence, the macroscopically monitored values of the luminescence-optical parameters (luminescence quantum efficiency, luminescence decay time) will undergo a particularly efficient change if a substantial number of molecules of the two substances are brought into close contact with each other.

To obtain close spatial contact, AT 393 035 proposes a covalent bonding of donor and acceptor molecules. In EP 214 768 individual donor and acceptor molecules are covalently attached to the surface of a joint substrate, such as glass.

The main disadvantage of a covalent bond between donor and acceptor molecules is that considerable synthesis efforts are required to produce covalent bonds between desirable luminophores and suitable pH- or ion-sensitive chromophores.

Considerable efforts are further needed to covalently attach donor and acceptor molecules to the surface of a joint substrate, with the additional drawback of the negative effects boundary surface phenomena have on the quality of the measured results.

SUMMARY OF THE INVENTION

It is an object of the present invention to propose a sensor layer in which the chemical synthesis efforts needed to obtain the spatial proximity of a substantial number of donor and acceptor molecules are minimized and negative influences of boundary surface effects are avoided.

In the invention, this object is achieved by providing that luminophore and chromophore be ionic substances of differing electrical charges, which are present as ion pairs in a matrix material that is permeable to the chemical component being determined.

It is provided in a first variant of the invention that the matrix material have an anionic chromophore and a cationic luminophore, where n chromophore molecules of the charge number −m and m luminophore molecules of the charge number +n form a n:m ionic pair, while it is provided in a second variant that the matrix material have a cationic chromophore and an anionic luminophore, where n chromophore molecules of the charge number +m and m luminophore molecules of the charge number −n form a n:m ionic pair.

As is seen in the following examples, it is much easier to produce ion pairs than complex molecules using multistep synthesis.

According to the invention, desirable luminophores (donor) are characterized by high luminescence quantum efficiency and long luminescence decay time (>100 ns). Preferred luminophores are cationic, metalorganic complexes of palladium, rhodium, platinum, ruthenium, osmium, rare earths (in particular, europium and lanthanum). The organic portion of these metalorganic complexes may consist of ligands from the group of porphyrins, bipyridyls, phenanthrolines or other heterocyclical compounds.

Preferred pH- and cation-sensitive chromophores (acceptor) are anionic substances whose light absorption will change upon direct or indirect chemical/physical interaction with the sample component to be determined, and whose absorption spectrum overlaps the emission spectrum of the luminophore, at least partially.

I) Determination of the pH Value of a Sample

State-of-the-art optical sensors for pH determination (cf M. J. P. Leiner and O. S. Wolfbeis, "Fiber Optic pH Sensors" in O. S. Wolfbeis, "Fiber Optic Chemical Sensors and Biosensors", CRC-Press, Boca Raton, 1991, Vol.I, Chapter 8) usually contain an absorption dye (chromophore) or fluorescent dye incorporated in an ion-permeable, preferably hydrophilic polymer matrix. In dependence of the pH value (pH=−log(aH+)) of the sample medium a thermodynamic equilibrium is established between the protonated and deprotonated forms of the chromophore or fluorophore. From the concentration ratio of the two forms measured by optical methods the pH value of the sample medium may be obtained.

Reaction:

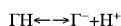

$\Gamma H$ is the protonated, and $\Gamma^-$ the deprotonated form of the chromophore. $H^+$ denotes a proton.

In AT 393 035 referred to above, pH-sensitive chromophores are described, which are attached, preferably covalently, to a pH-insensitive luminophore (donor). From the luminescence decay time of the luminophore (L) the pH value of the test solution is obtained.

Reaction:

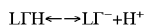

For luminescence-optical pH-determination as proposed by the invention, n:m ion pairs $\{n(\Gamma H)^{-m}mL^{+n}\}$ consisting of an anionic, pH-sensitive chromophore $(\Gamma H^{-m})$ with the charge number −m and a cationic, pH-insensitive luminophore $(L^{+n})$ with the charge number +n are used, which are incorporated in a hydrophilic polymer matrix.

Reaction:

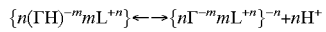

In the instance of low pH values (pH<<pKa of the chromophore) of the sample medium, the chromophore is present in fully protonated form. Due to the minimal spectral overlap of the absorption band of the deprotonated chromophore and the emission band of the luminophore the nonradiative energy transfer rate from luminophore to chromophore reaches a minimum. Correspondingly, the values of mean luminescence decay time and relative luminescence intensity of the luminophore reach a maximum.

In the instance of high pH values (pH>>pKa of the chromophore) of the sample medium, the chromophore is present in fully deprotonated form. Due to the maximal spectral overlap of the absorption band of the deprotonated chromophore and the emission band of the luminophore the nonradiative energy transfer rate from luminophore to chromophore reaches a maximum. Correspondingly, the values of mean luminescence decay time and relative luminescence intensity of the luminophore reach a minimum.

For pH values of the sample medium in the range of +/−1.5 pH units of the pKa value of the chromophore, the mean luminescence decay time or relative luminescence intensity of the luminophore will supply a sufficiently accurate pH value of the sample medium.

II) Determination of the Concentrations and/or Activities of Cations and Anions in a Sample ($Li^+$, $Na^+$, $K^+$, $Mg^{++}$, $Ca^{++}$, $Cl^-$)

Previous optical sensors and processes for determining the concentrations and/or activities of cations in a sample medium employ different methods. For example, the above mentioned publication AT 393 035 is concerned with cation-sensitive chromophores $(\Gamma^-)$ which are attached, preferably covalently, to a cation-sensitive luminophore (L).

Reaction:

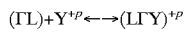

Y is the cation being determined, with the charge number +p.

According to the invention, cation-sensitive chromophores $(\Gamma^{-m})$ have at least one anionic group of the charge number −m, which will permit them to form a n:m ionic pair with a cationic luminophore $(L^{+n})$ of the charge number +n.

Reaction:

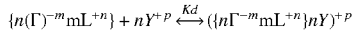

Y is the cation being determined, with the charge number +p, and Kd is the dissociation constant of the cation-sensitive chromophore.

In the instance of very high cation concentrations ($cY^+_p$>>Kd of the chromophore) of the sample medium the chromophore is present in fully complexed form. In the instance of very low cation concentrations ($cY^{+p}$<<Kd of the chromophore) of the sample medium the chromophore is present in free, noncomplexed form.

If the logarithmic concentration $\log(cY^{+p})$ of the interesting cation of the sample medium is in the range of $\log(Kd)$ +/−1.5, the concentration of the respective cation in the sample medium may be inferred with sufficient accuracy from the mean luminescence decay time and/or relative luminescence intensity of the luminophore.

Further optical measuring methods and sensors for determining the concentrations and/or activities of cations are described in U.S. Pat. No. 4,645,744, EP 0 358 991 B1, and EP 0 461 392 A2, for instance, where a pH-sensitive chromophore ($\Gamma H$), or a pH-sensitive luminophore and a neutral ionophore (I) are provided in a substantially hydrophobic polymer matrix. According to the disclosed measuring method, cations ($Y^{+p}$) are exchanged with the sample medium (for example, $K^+$ for $H^+$ or $Ca^{++}$ for $2H^+$). As a consequence, the measured results are dependent on the pH value of the sample medium. Such measuring methods are suitable under conditions in which the pH value of the sample medium is known or may be adjusted to a known value by means of a pH buffering layer.

Reaction:

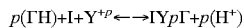

Y is the cation being determined, +p its charge number.

In further development of these methods the invention proposes that for determination of the cationic concentration of a sample provisions be made for n:m ion pairs $\{n(\Gamma H)^-_mmL^{+n}\}$ consisting of an anionic, pH-sensitive chromophore $((\Gamma H)^{-m})$ with the charge number −m and a cationic, pH-insensitive luminophore $(L^{+n})$ with the charge number +n, as well as for a neutral ionophore (I) that is selective for the cation being determined, which are incorporated in a hydrophobic polymer matrix.

Reaction:

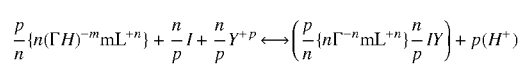

Y is the cation being determined, +p is its charge number.

Examples of neutral ionophores suitable for the purposes of the invention are listed in Table 2, examples of suitable chromophores in Table 1. Example 3 is a description of how a potassium-sensitive sensor is prepared. The respective measurement results are given in FIG. 3.

Publications EP 9 358 991 B1 and Anal.Chim.Acta 255 (1991), p.35–44 describe optical sensors for determining anions, such as Cl⁻, where the anion to be determined is co-extracted from the sample medium together with a cation (for example, Cl⁻ and H⁺). In that instance a lipophilic, pH-sensitive chromophore (fluorescein derivative) and an optically inactive, cationic substance ($Q^+$) are incorporated in a substantially hydrophobic polymer matrix.

In dependence of the H⁺ and Cl⁻ concentration of the sample medium the pH-sensitive chromophore (ΓH) in the polymer matrix is present in protonated and/or deprotonated form. Absorption of the deprotonated form will rise with a growing degree of deprotonation. The degree of deprotonation (and hence, absorption) depends on the pH value and concentration of the anion being determined. The pH value of the sample medium must be known or adjusted to a known value, so as to indicate the concentration of the anion being determined.

Reaction:

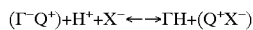

$X^-$ is the anion being determined.

In further development of the method disclosed here the invention proposes, for example, when the chloride concentration of a sample is to be determined, that n:m ion pairs $\{n(\Gamma^-Q^+)^{-m}mL^{+n}\}$ be provided, consisting of an anionic, deprotonated, pH-sensitive chromophore $((\Gamma)^{-(m+1)})$ with the charge number $-(m+1)$ combined with a lipophilic, cationic substance ($Q^+$) with the charge number +1, hence an overall charge number $-m$, and a cationic, pH-insensitive luminophore ($L^{+n}$) with the charge number +n, which are supplied in a hydrophobic polymer matrix that is permeable to chloride ions of the sample by coextraction. The lipophilic substance ($Q^+$) could be a quaternated ammonium compound, for instance.

Reaction:

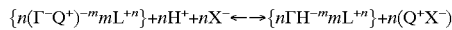

m being the charge number of the protonated, anionic chromophore, and n the charge number of the cationic luminophore.

Examples of pH-sensitive chromophores according to the invention are listed in Table 1. In the instance of low pH values and high chloride concentrations of the sample medium the pH-sensitive chromophore preferably is supplied in protonated form; the optically inactive, cationic substance forms a Cl⁻ counterion in the matrix. Absorption of the deprotonated form of the chromophore reaches a minimum. The values of mean luminescence decay time and relative luminescence intensity of the luminophore reach a maximum.

In the instance of high pH values and low chloride concentrations of the sample medium the pH-sensitive chromophore preferably is present in deprotonated form, the optically inactive, cationic substance compensating the negative charge generated by dissociation of the proton. Absorption of the deprotonated form of the chromophore reaches a maximum. The values of mean luminescence decay time and relative luminescence intensity of the luminophore reach a minimum.

If the pH value of the sample medium is known, the values obtained for mean luminescence decay time and relative luminescence intensity of the luminophore may be used to indicate the chloride concentration of the sample medium.

According to the invention it will also be possible, for example, for determination of the chloride concentration of a sample, to provide n:m ion pairs $\{n\Gamma^{-m}mL^{+n}\}$ consisting of an anionic, deprotonated, pH-sensitive chromophore ($\Gamma^{-m}$) with the charge number $-m$ and a cationic, pH-insensitive luminophore ($L^{+n}$) with the charge number +n, which are supplied in a hydrophobic polymer matrix that is permeable to chloride ions of the sample by coextraction. The optically inactive, cationic substance ($Q^+$) is replaced by the cationic luminophore:

Reaction:

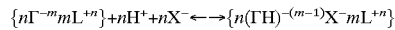

m being the charge number of the deprotonated, anionic chromophore, and n the charge number of the cationic luminophore.

III) Determination of Components of Liquid or Gaseous Sample Media, which Exhibit Weak Acid or Basic Reactions in Aqueous Environments and are Gaseous under Normal Conditions Determination of $CO_2$ Optical sensors for determination of the $CO_2$ partial pressure of a liquid or gaseous sample medium usually comprise a reaction space which is separated from the specimen by an ion-impermeable, gas-permeable material. The reaction space is often identical with the indicator substrate material of an optical pH sensor. In addition, the reaction space usually includes one or several pH buffering substances, such as carbonates, phosphates, and/or organic compounds exhibiting acid or basic reactions in aqueous media. As a consequence, $pCO_2$ determination of the sample medium may be performed by optical pH determination.

In a variant of this measuring principle described in EP-A 0 205 870, the reaction space is provided in the shape of "droplets" in ion-impermeable, gas-permeable, polymer material.

Reaction:

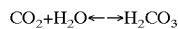

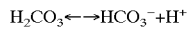

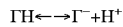

In further development of the luminescence-optical determination of $CO_2$ as proposed by the invention, n:m ion pairs $\{n(\Gamma H)^{-m}mL^{+n}\}$ are provided, consisting of an anionic, pH-sensitive chromophore ($\Gamma H^{-m}$) with the charge number $-m$ and a cationic, pH-insensitive luminophore ($L^{+n}$) with the charge number +n, which are present in aqueous buffer solution, in a reaction space that is separated from the sample medium by an ion-impermeable, gas-permeable material.

Reaction:

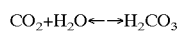

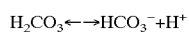

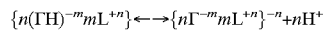

Under the invention, $CO_2$ determination by means of the sensors described above, comprising a reaction space with an aqueous pH buffer and an ion-impermeable, gas-permeable material separating the reaction space from the sample medium, is performed by pH determination in the reaction space of the sensor (see Examples 1 and 2). High $CO_2$ values of the sample medium correspond to low pH values of the reaction space, and low $CO_2$ values of the sample medium correspond to high pH values of the reaction space.

An alternative method of optical $CO_2$ determination, for which only a single reaction space and no aqueous pH buffering substances are required, is described by Mills et al., Anal.Chem. 64, 1992, 1383–1389. In that case the deprotonated form of a pH-sensitive chromophore with an optically inactive, cationic substance ($Q^+$) is present in a reaction space consisting of essentially ion-impermeable, gas-permeable, polymer material. $CO_2$ from the sample diffuses into the polymer material, where it is hydrated and reacts in a chemical equilibrium reaction with the deprotonated form of the chromophore and the optically inactive substance. From the light absorption of the deprotonated form of the chromophore the $CO_2$ partial pressure of the sample medium is inferred.

Reaction:

$$CO_2 + H_2O \leftrightarrow H_2CO_3$$

$$(I^-Q^+) + H_2CO_3 \leftrightarrow (Q^+HCO_3^-) + IH$$

In a variant of the invention concerned with luminescence-optical $CO_2$ determination n:m ion pairs $\{n(I^-Q^+)^{-m}mL^{+n}\}$ are provided, which consist of an anionic, deprotonated, pH-sensitive chromophore $((I)^{-(m+1)})$ with the charge number $-(m+1)$ combined with a lipophilic, cationic substance ($Q^+$) with the charge number +1, hence an overall charge number $-m$, and a cationic, pH-insensitive luminophore ($L^{+n}$) with the charge number $+n$, which are supplied in a hydrophobic polymer matrix that is impermeable to ionic substances in the case of aqueous sample media.

Reaction:

$$CO_2 + H_2O \leftrightarrow H_2CO_3$$

$$\{n(I^-Q^+)^-mL^{+n}\} + nH_2CO_3 \leftrightarrow n(Q^+HCO_3^-) + (n(IH)^{-m}mL^{-n})$$

m being the charge number of the protonated, anionic chromophore, and n the charge number of the cationic luminophore.

In accordance with the invention, $CO_2$ determination by means of a sensor comprising a reaction space without aqueous buffering substances, is based on the determination of the ratio of the protonated and deprotonated forms of a pH-sensitive chromophore.

In the instance of very low $CO_2$ values of the sample medium the chromophore preferably is provided in deprotonated form, forming a ionic bond with the optically inactive, cationic substance in the matrix. Absorption of the deprotonated form of the chromophore reaches a minimum. The values of mean luminescence decay time and relative luminescence intensity of the luminophore reach a maximum.

In the instance of high $CO_2$ values of the sample medium the chromophore is provided in protonated form. The optically inactive, cationic substance forms a ionic bond with hydrogen carbonate. Absorption of the deprotonated form of the chromophore reaches a minimum. The values of mean luminescence decay time and relative luminescence intensity of the luminophore reach a minimum.

According to the invention it will also be possible to provide n:m ion pairs $\{nI^{-m}mL^{+n}\}$, consisting of an anionic, deprotonated, pH-sensitive chromophore ($I^{-m}$) with the charge number $-m$ and a cationic, pH-insensitive luminophore ($L^{+n}$) with the charge number $+n$, which are supplied in a hydrophobic polymer matrix that is impermeable to ionic substances in the instance of aqueous sample media. unlike in the example referred to before, the optically inactive, cationic substance ($Q^+$) is replaced by the cationic luminophore in this case:

Reaction:

$$\{nI^{-m}mL^{+n}\} + nH_2CO_3 \leftrightarrow \{n(IH)^{-m}n(HCO3)^-mL^{+n}\}$$

m being the charge number of the deprotonated, anionic chromophore, and n the charge number of the cationic luminophore.

Determination of $NH_3$

The determination of NH3, as an example of a component exhibiting a basic reaction in aqueous environment, may be effected in a way similar to the determination of $CO_2$ according to Mills (T. Werner et al., Analyst 120, 1995, 1627–1631). No optically inactive, cationic substance is required.

Reaction:

$$IH + NH_3 \leftrightarrow (I^-NH_4^+)$$

According to the invention the determination of $NH_3$ is effected in the same way as the $CO_2$ determination described above.

Reaction:

$$\{n(IH)^{-m}mL^{+n}\} + nNH_3 \leftrightarrow (n\{I^{-m}mL^{+n}\}^-nNH_4^+)$$

pH-sensitive Chromophores Suitable for use with the Invention

Ion pairs in accordance with the invention, consisting of anionic, pH-sensitive chromophores from Table 1 and suitable cationic luminophores from Table 3 are obtained as described in Examples 1a and 2a. The preparation of pH sensors using these ion pairs in accordance with the invention is described in Examples 1b (ion-permeable sol-gel matrix) and 2b (ion-permeable hydrogel matrix). The respective measurement data (mean luminescence decay time, relative luminescence intensity) are displayed in FIGS. 1 and 2, in dependence of the pH value of the sample medium.

TABLE 1 pH-sensitive Chromophores

| Chromophore | Absorption wavelength [nm] protonated/deprotonated | pKa |
|---|---|---|
| Triphenylmethane dyes | | |
| Bromophenol blue | 430/617 | 3.8 |
| Bromothymol blue | 430–435/615–618 | 6.7 |
| Dibromoxylenol blue | 420/614 | 7.6 |
| Azo dyes | | |
| Calmagit | 530/605 | 8.0 |
| Nitrazine yellow | 460/590 | 6.5 |
| Others | | |
| o-chlorophenol-indophenol | 555/625 | 7.1 |
| Naphthol-phthalein | 428/661 | 6.7, 7.9 |

In addition, pH-sensitive triphenylmethane dyes of the general form

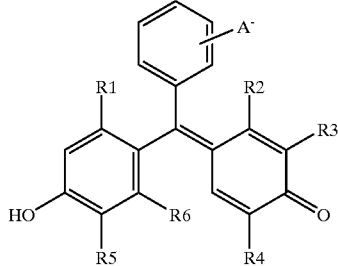

are used, $A^-$ standing for the deprotonated form of a strong acid, such as $SO_3^-$ or $—COO^-$, and R1–R6 for halogen atoms, nitro groups or alkyl groups; as well as pH-sensitive azo dyes of the general form

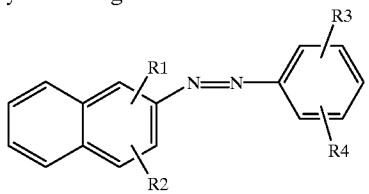

R1–R4 standing for substituents, such as halogen atoms, nitro groups or alkyl groups, while at least one —OH group and one —$SO_3^-$ or —$COO^-$ group must be provided.

Cation-sensitive Chromophores Suitable for use with the Invention

Examples of cation-sensitive chromophores for determination of lithium, potassium, sodium, magnesium and calcium ions include anionic azo dyes, stilbene dyes and merocyanines, which contain at least one anionic group and an ion-selective crown ether system, and whose absorption band with the longest wavelengths overlaps the emission band of the luminophore at least partially, the interaction with the alkali or alkaline-earth ions being determined leading to a spectral shift of the longest-wave absorption band.

Ionic bonds between anionic, cation-sensitive chromophores and cationic luminophores are obtained in the same way as the ionic bonds between anionic, pi-sensitive chromophores and cationic luminophores described by the invention (see Examples 1 and 2).

TABLE 2

Neutral Ionophores

| Ionophore | Ion |
|---|---|
| PTM14C4 (14-crown-4) **) | Li+ |
| Sodium Ionophore I-II *) | Na+ |
| Valinomycin | K+ |
| Magnesium Ionophore ETH 3832 *) | Mg++ |
| Calcium Ionophore I-IV *) | Ca++ |

*) Ionophores for Ion-Selective Electrodes and Optodes, Fluka Chemie AG, CH-9470 Buchs, Switzerland.
**) K. Watanabe et al. Anal. Chem. 65, 1993.

Other central atoms used are Ir, Rh, Pd, Pt, Re. In order to obtain ion pairs of the general form $\{n(IH)^{-m}mL^{+n}\}$ or $\{n(I^-)^{-m}mL^{+n}\}$ from anionic, pH- or ion-sensitive chromophores ($I^{-m}$) with cationic luminophores ($L^{+n}$), those chromophores or chromoionophores (ion-sensitive chromophores) may be used which contain an anionic group whose charge number does not change vis-a-vis the pH values of the sample material.

For example, the triphenylmethane dyes in Table 1 have a sulpho group which is present in the anionic form (R—$SO_3^-$) with the charge number –1 for pH values >3.

According to the invention it would also be possible to attach at least one anionic group of the general form –($CH_2$)$_x$—$A^{-n}$ (x=0–4; n=1,2) to those chromophores which do not contain this group.

Preferred anionic groups are derived from compounds exhibiting acid reactions in aqueous environment, such as sulphonic acids of the general form (R—$SO_3H$) and carbonic acids of the general form R—COOH.

Ion pairs offering special advantages in determining $CO_2$ (and chloride) include 1:1 ion pairs consisting of an anionic chromophore with the charge number –2 (Table 1, triphenylmethane dyes or azo dyes with at least one pH-active group and an anionic group) and a cationic luminophore with the charge number +2 (Table 3).

As is seen from the above, the ion pairs which are especially preferred by the invention for determination of $CO_2$ and anions (chloride) are identical, and are supplied in hydrophobic polymer materials that are substantially impermeable to ionic sample constituents. In anion determination (e.g., chloride) the anion being determined is coextracted into the polymer material with a cation ($H^+$), whereas in the instance of $CO_2$ and $NH_3$ the charge-neutral molecules will diffuse into the material regardless of the presence of any counterions. For gaseous samples it is thus evident that $CO_2$ determination is not affected by any anionic sample components. This is not true in general for aqueous samples, however. Hence, in order to avoid interferences in $CO_2$ determination caused by anionic components of aqueous samples, it is provided that the sensor layer be covered by a gas-permeable layer which does not contain the ion pair. Suitably materials feature high permeability to the gaseous components to be determined, for example, teflon.

Essentially Hydrophobic, Ion-impermeable Matrices

To obtain sensors as proposed by the invention, which exchange the cation being determined (such as $K^+$) with a proton of the sample medium, or coextracted the anion being determined (such as $Cl^-$) with a proton of the sample medium, polymer materials are suited that are substantially impermeable to ionic substances of the sample medium.

TABLE 3

Cationic Luminophores

| Luminophore (L) | Abbrev. | Absorption maximum (nm) | Luminescence maximum (nm) |
|---|---|---|---|
| [(Ru(II)-tris-(2,2'-bibyridyl)]$^{2+}$ | Ru(bpy)$_3^{2+}$ | 452 | 628 |
| [(Ru(II)-tris-(4,4'-diphenyl-2,2'-bipyridyl)]$^{2+}$ | Ru(dph-bpy)$_3^{2+}$ | 474 | 632 |
| [(Ru(II)-tris-(1,10-phenanthroline)]$^{2+}$ | Ru(phen)$_3^{2+}$ | 447 | 604 |
| [(Os(II)-bis-(terpyridine)]$^{2+}$ | | 510 | 729 |
| [(Os(II)-tris-(1,10-phenanthroiine)]$^{2+}$ | | 650 | 690 |

These materials are also suitable for preparing sensors according to the invention which are used for determination of gases or gaseous components in liquid sample media.

Preferred are all essentially hydrophobic polymers that are soluble in organic solvents, such as polyvinyl chloride, polystyrenes, polycarbonates, polyethylenes, polyurethanes, silicones, copolymers of polyvinyl alcohol and polyvinyl acetate, and copolymers of polyvinyl chloride, polyvinyl alcohol and polyvinyl acetate.

To these materials up to 80 percent by weight plasticizers may be added, such as dioctyl sebacate, tris-(2-ethylhexyl)-phosphate, 2-nitrophenyl-octyl-ether, 2-nitrophenyl-butyl-ether.

Essentially Hydrophilic, Ion-permeable Matrices

To obtain sensors exhibiting pii- and ion-sensitive chromophores as proposed by the invention, hydrophilic, ion-permeable polymers are preferred.

Representatives are nafion, cellulose, and cellulose acetates. An important group of hydrophilic polymers are the so-called hydrogels. Relevant examples are polyurethanes with hydroxylic groups, polyhydroxyethylmethacrylates, crosslinked polyvinyl alcohols, and polyacrylamides.

Moreover, incorporation into sol-gels will yield pH- and ion-permeable materials. Sol-gels are porous, organically produced, vitreous materials based on silicon compounds or titanium-organic compounds. The most typical representative is a sol-gel made from tetraethoxyorthosilane.

The use of ion-permeable materials for gas sensors in accordance with the invention is possible if the gas-sensitive material is separated from a liquid sample medium by an additional material consisting of ion-impermeable, gas-permeable polymers, such as teflon or silicones.

EXAMPLE 1

(a) Preparation of a 2:1 Ion Pair of the General form $\{n(TH)^{-m}mL^{+n}\}$ using Bromothymol Blue and $Ru(phen)_3^{2+}$ 129.2 mg bromothymol blue sodium salt (200 mmole) is dissolved in 3 ml 0.1 N NaOH and 20 ml water. After adding 4 ml of 0.1 N HCl and a solution of 82.1 mg [Ru(II)-tris(1, 10-phenanthroline)]$Cl_2.6H_2O$ (100 mmole) in 3 ml water, the ion pair is obtained as orange precipitate. The latter is filtered off by suction, rinsed with water and dried over NaOH. Yield: 80 percent; melting point: 237° C. Data of elementary analysis (computed/found): C:54.14/55.68, H:4.54/4.64, N:4.21/4.28.

(b) Preparation of a pH-sensitive Sensor Layer 3 mg ketyltrimethyl ammonium chloride and 3 mg of the 2:1 ion pair $\{2(\text{bromothymol blue})^{1-} Ru(phen)_3^{2+}\}$ is dissolved by ultrasound in 1 ml methanol. After adding 200 µl tetramethoxysilane and 100 µl of a 0.1 N hydrochloric acid, the mixture is allowed to gellate for 5 days in snap-cover jars. This material is used for sensor films which are applied on optically transmissive substrate material (polyester), or for coating optical fibers. The sensors must be left to dry for several days at 40° C.

FIG. 1 displays the dependence of mean decay time $t_m$ on the pH value of the sample medium.

EXAMPLE 2

(a) Preparation of a 2:1 Ion Pair of the General form $\{n(TH)^{-m}mL^{+n}\}$ using $Ru(dph\text{-}bpy)_3^{2+}$ and Bromothymol Blue 129.2 mg bromothymol blue sodium salt (200 mmole) is dissolved in 3 ml of 0.1 N NaOH and 20 ml water. Diluted hydrochloric acid is added until the indicator changes to acid form. This solution is added dropwise to a saturated aqueous solution of the ruthenium complex [Ru(II)-tris(4,4'-diphenyl-2,2'-bipyridyl)]$Cl_2$ by continuous stirring. The ion pair is obtained as orange precipitate. The latter is filtered off by suction, rinsed with water and dried over NaOH. Yield: 80 percent. Data of elementary analysis (computed/found): C:61.99/60.38, H:4.64/4.61, N:3.61/3.87.

(b) Preparation of a pH-sensitive Sensor Layer

To obtain a 5 percent hydrogel solution, 4 g of hydrogel D4 produced by Tyndale-Plains Hunter Ltd., Ringoes, N.Y. 08551, is dissolved in 72 ml EtOH and 8 ml $H_2O$ by stirring within 5 hours.

10 g of this solution is added to 5.82 mg of the 2:1 ion pair $\{2(\text{bromothymolblue})^{1-} Ru(dph\text{-}bpy)_3^{2+}\}$ and stirred until a homogeneous, clear solution is obtained.

From this solution sensor films are prepared which are applied on optically transmissive substrate material (polyester), where they are left to dry for several hours at room temperature, until evaporation of the solvent is complete.

Figure 2:
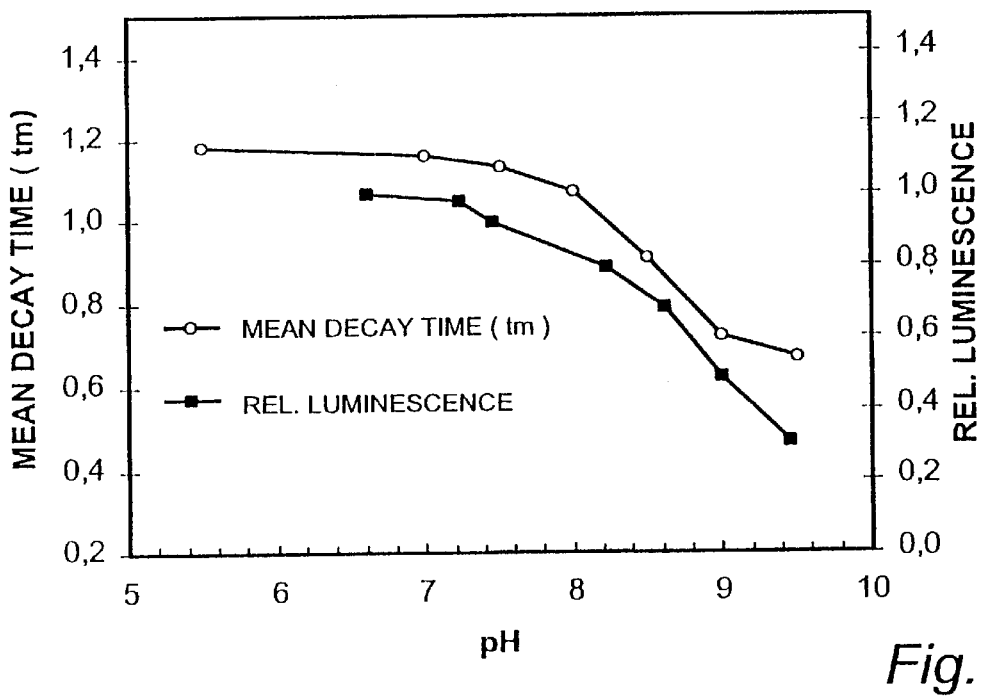
FIG. 2 displays the dependence of mean decay time $t_m$ and relative luminescence intensity of the pH value of the sample medium of Example 2.

FIG. 2 displays the dependence of mean decay time $t_m$ and relative luminescence intensity on the pH value of the sample medium.

EXAMPLE 3

Preparation of a Potassium-sensitive Sensor Layer 2.7 mg of the 2:1 ion pair $\{(\text{bromothymol blue})^{1-} Ru(dph\text{-}bpy)_3^{2+}\}$, and 3.8 mg valinomycin, together with 100 mg dioctyl sebacate and 50 mg PVC is dissolved in 3 ml tetrahydrofurane. This mixture is used for preparing sensor films or coating optical fibers. The sensors are stored in a dry place and activated in buffer solution for at least 8 hours before measurement.

Figure 3:
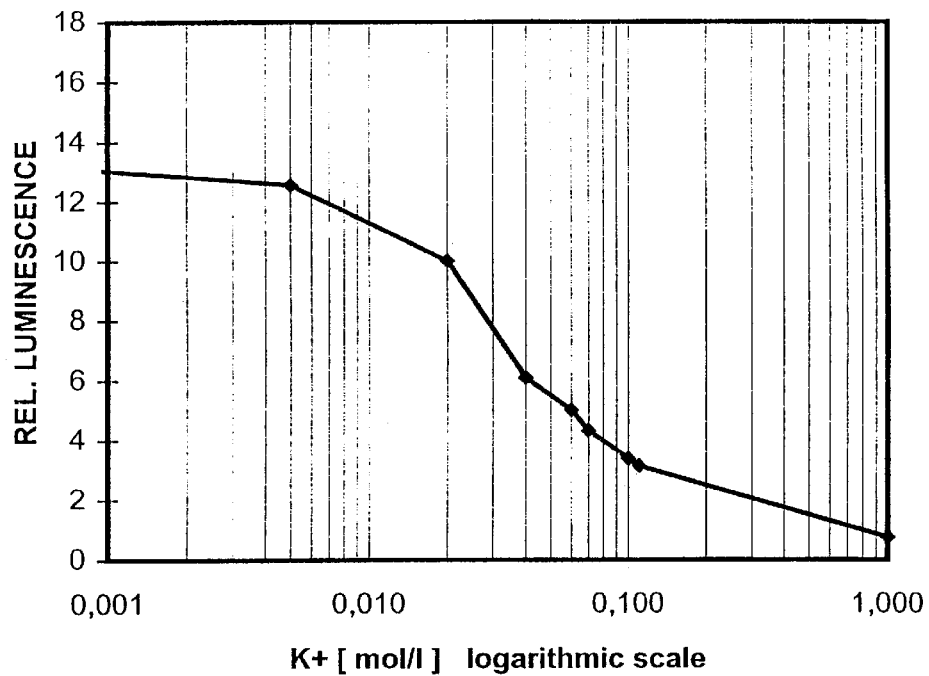
FIG. 3 displays the dependence of relative luminescence intensity on the $K^+$ concentration of the sample medium of Example 3.

FIG. 3 displays the dependence of relative luminescence intensity on the $K^+$-concentration of the sample medium.

Figure 4:
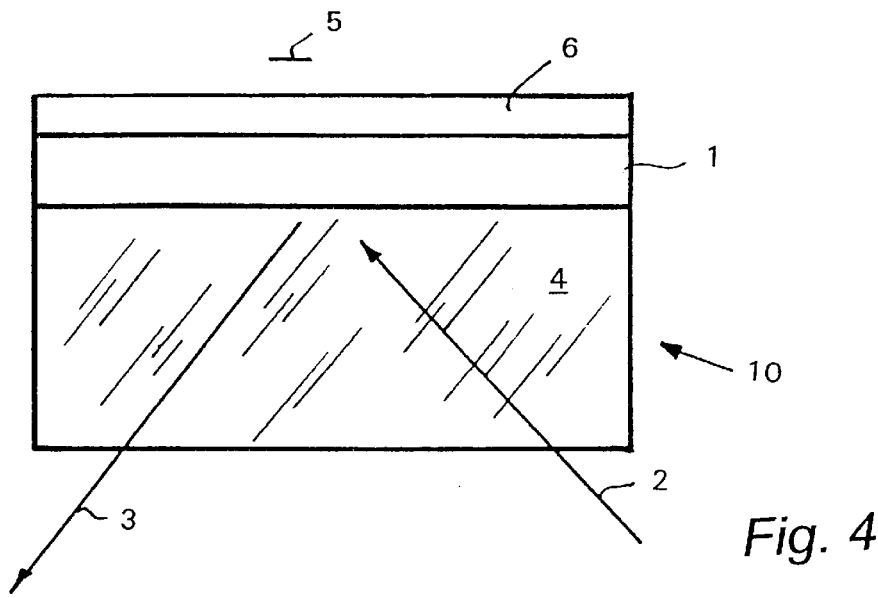
FIG. 4 shows the proposed sensor layer of a sensor in sectional representation.

In FIG. 4 the proposed sensor layer 1 of a sensor 10 shown schematically in sectional representation, is applied on a substrate 4 that is transmissive to excitation and emission radiation 2,3. In the sensor layer 1, which consists of a matrix material that is permeable to the interesting chemical component of the sample 5, the ionic luminophore and the ionic chromophore are immobilized. On the side of the sample the sensor layer 1 may have a cover layer 6.

According to the invention, the sensor layer 1 could also be provided at the end of an optical fiber guide.

We claim:

1. Luminescence-optical method for quantitative determination of at least one chemical component of a gaseous or liquid sample employing a chromophore which is directly or indirectly responsive to the component being determined by changing its absorption spectrum and a luminophore which is not responsive to the component being determined, the emission spectrum of the luminophore overlapping the absorption spectrum of the chromophore at least partially, and the change in at least one luminescence characteristic of the luminophore, which is effected by the energy transfer between luminophore and chromophore, being used for quantitative determination of the chemical component, wherein luminophore and chromophore are ionic substances of differing electrical charges, which are incorporated as ion pairs in a matrix material that is permeable to the chemical component being determined, and wherein the matrix material is brought into contact with the sample.

2. Method as claimed in claim 1, wherein an anionic chromophore and a cationic luminophore are used, n chromophore molecules of the charge number −m and m luminophore molecules of the charge number +n forming a n:m ionic pair.

3. Method as claimed in claim 1, wherein a cationic chromophore and an anionic luminophore are used, n chromophore molecules of the charge number +m and m luminophore molecules of the charge number −n forming a n:m ionic pair.

4. Method as claimed in claim 1, wherein the change in luminescence decay time of the luminophore due to energy transfer, is employed for determining the concentration, activity or partial pressure of the chemical component in the liquid or gaseous sample.

5. Method as claimed in claim 1, wherein the change in luminescence intensity of the luminophore due to energy transfer, is employed for determining the concentration, activity, or partial pressure of the chemical component in the liquid or gaseous sample.

\* \* \* \* \*